US008235044B2

(12) United States Patent
Fletcher

(10) Patent No.: US 8,235,044 B2
(45) Date of Patent: Aug. 7, 2012

(54) INHALER VALVE

(75) Inventor: Ian Fletcher, Loughborough (GB)

(73) Assignee: Astrazeneca AB, Södertälje (SE)

( * ) Notice: Subject to any disclaimer, the term of this patent is extended or adjusted under 35 U.S.C. 154(b) by 914 days.

(21) Appl. No.: 11/997,437

(22) PCT Filed: Jul. 31, 2006

(86) PCT No.: PCT/SE2006/000919
§ 371 (c)(1),
(2), (4) Date: Dec. 5, 2008

(87) PCT Pub. No.: WO2007/015665
PCT Pub. Date: Feb. 8, 2007

(65) Prior Publication Data
US 2009/0211578 A1    Aug. 27, 2009

(30) Foreign Application Priority Data
Aug. 1, 2005    (SE) ...................................... 0501766

(51) Int. Cl.
*A62B 7/00*    (2006.01)
(52) U.S. Cl. .......... 128/205.22; 128/200.14; 128/200.23
(58) Field of Classification Search ............ 128/200.14, 128/200.23
See application file for complete search history.

(56) References Cited

U.S. PATENT DOCUMENTS

| 5,702,362 | A | 12/1997 | Herold et al. | |
| 7,168,597 | B1 * | 1/2007 | Jones et al. | 222/402.2 |
| 7,721,731 | B2 * | 5/2010 | Bacon | 128/200.23 |
| 7,793,805 | B2 * | 9/2010 | Allsop | 222/402.2 |
| 2001/0013342 | A1 * | 8/2001 | Burns | 128/200.23 |
| 2004/0123865 | A1 | 7/2004 | Haikarainen et al. | |
| 2006/0180148 | A1 | 8/2006 | Beller | |

FOREIGN PATENT DOCUMENTS

| DE | 10300032 | 5/2004 |
| EP | 0166294 | 1/1986 |
| EP | 0744188 | 11/1996 |
| WO | WO 92/09322 | 6/1992 |
| WO | WO 93/03785 | 3/1993 |

* cited by examiner

*Primary Examiner* — Glenn Richman
(74) *Attorney, Agent, or Firm* — Finnegan, Henderson, Farabow, Garrett & Dunner, LLP

(57) ABSTRACT

Rotary metering valve (200) with a valve inlet (260), a valve outlet (270) and a rotary valve member (280) for transferring a metered dose of aerosol formulation from the inlet to the outlet, wherein the rotary valve member is provided with an inlet port (290) and an outlet port (300), both in communication with a metering conduit (310) in the rotary valve member, the rotary valve member in sequence being rotatable between at least three positions:

inlet position where the inlet port is in communication with the valve inlet and aerosol formulation enters the metering conduit, metering position where both ports are closed preserving a metered volume of aerosol formulation in the metering conduit, outlet position where the outlet port is in communication with the valve outlet and the metered dose of aerosol formulation is dispensed from the valve.

46 Claims, 10 Drawing Sheets

INHALER VALVE

RELATED APPLICATIONS

The present application is a U.S. National Phase Application of International Application No. PCT/SE2006/000919 (filed Jul. 31, 2006) which claims the benefit of Sweden Patent Application No. 0501766-0 (filed Aug. 1, 2005), both of which are hereby incorporated by reference in their entirety.

The present invention relates to the art of inhaler devices, and in particular to an inhaler valve of rotary type, and to a method of filling such.

BACKGROUND OF THE INVENTION

Many types of drugs are provided in fluid form, such as a solution or suspension or emulsion of drug in a propellant, an aerosol propellant, and are adapted for oral inhalation by a patient. As one example, a container might contain asthma medicine such as fluticasone propionate. During a typical manufacturing process, the container is sealed by crimping a metering valve onto the neck of the container. The container is then charged through the valve with the aerosol propellant.

In order to deliver the drug to the patient, the container operates in conjunction with an actuator as a system commonly known as a metered dose inhaler (MDI) system. The actuator includes a housing having an open container-loading end and an open mouthpiece. A nozzle element is disposed within the housing and includes a valve stem-receiving bore communicating with a nozzle orifice. The orifice is aimed toward the mouthpiece. In order to receive a properly metered dosage of medicine from the container, the patient installs the container into the actuator through the container-loading end until the valve stem is fitted into the receiving bore of the nozzle element. With the container so installed, the opposite end of the container typically extends to some degree outside the actuator housing. The patient then places the mouthpiece into his or her mouth and actuates the valve. Owing to the design of the valve, the design of the nozzle element and the pressure differential between the interior of the container and the ambient air, a short burst of precisely metered, atomized formulation is thereby delivered to the patient.

FIG. 1 shows a sectional view of one embodiment of a conventional inhaler container 10 (can). The inhaler 10 is comprised of a can 20 and a linear metering valve assembly 30. The metering valve assembly is basically comprised of a valve mechanism 40 with a valve body 90, a valve stem 100, a valve spring 125, a gasket 50, a ferrule 60, and a support ring 70. Further, there is an opening 130 in the valve body 90, through which the drug enters the valve. In FIG. 1 and all following figures, the inhaler container 10 is shown in the operating position, i.e. with the valve directed downwards. As can be seen in FIG. 1 the valve assembly 30 is attached to the container 20 by a crimp 80, i.e. the upper section of the ferrule 60 is crimped in a crimping apparatus so that it closely clasps the lower section of the container 20. Further, the inhaler can 10 is sealed by the upper edge of the container 20 being pressed against the gasket 50 by the crimp 80. A metering chamber 110 is provided in order for the valve to deliver a metered volume upon actuation. In the rest position, a first seal 150 seals of the metered volume from the surrounding atmosphere, and a small gap between the valve stem 100 and a secondary seal 140 allows the content in the can 20 to enter the metered volume. When actuating the valve 30, the valve stem moves further into the valve body 90, first causing a wider section of the valve stem to enter the seal 140 sealing off the metered volume from the interior of the can, where after a stem bore 120 passes the seal 150 into the metered volume and the pressurized aerosol propellant in the metered volume is discharged via the valve stem 100.

Metering valves 30 of linear type dominates the metering valve market and essentially all inhaler actuators are adapted to this type of metering valve. However, this type of valve has a number of drawbacks, such as a relatively high actuation force that is related to the spring 125, the friction between the valve stem and the seals 140 and 150 and the pressure in the can, and that filling of a container involves the step of forcing the drug and propellant mixture through the seals. Furthermore, linear valves are comprised of a relatively large number of parts that have to be made with high accuracy in order for the valve to work properly and not leak.

U.S. Pat. No. 5,772,085 disclose in one embodiment a rotary metering valve, wherein a valve stem is capable of rotary motion. The valve comprises a nozzle block having a wide passage in communication with an aerosol vial. The nozzle block has an outlet passage for discharge of the pressurised aerosol formulation. An elastomeric sealing element is positioned within the nozzle block and is fixed relative to the nozzle block. A chamber is defined by the inside walls of the elastomeric sealing element. A valve stem is mounted within the sealing element and is capable of rotary movement about an axis. The valve stem has a recess with an opening. In the non-dispensing position there is open communication between the passage and the recess allowing free access of aerosol formulation. As the valve stem is rotated, the opening moves out of line with the passage and thus the opening is blocked by the sealing element thereby forming a closed volume within the recess. Further rotation of the valve stem will bring the opening into communication with the discharge passage thereby allowing the contents of the recess to be discharged under the influence of the aerosol propellant. This valve has neutral bias since there is no spring biasing means and the pressure of the aerosol formulation does not exert a bias. In a modification the valve stem comprises a plurality of recesses circumferentially arranged such that they may be sequentially filled and the contents dispensed by further rotation of the valve stem.

This valve, though simple in appearance, is relatively difficult to make leak proof at the high pressures present in the canister and the large area sealing element, and moreover, as it comprises an elastomeric sealing element that surrounds the valve stem, it is relatively complex to assemble. Moreover, in the basic embodiment with one metering chamber in the form of a recess in the valve stem, the stem has to be rotated 180° in order to be actuated, While in the later proposed embodiment with a plurality of recesses, the sealing situation becomes even more critical and the benefit of free flow of the aerosol formulation in the canister discussed in U.S. Pat. No. 5,772,085 will be lost for the filled recesses waiting to be dispensed. Moreover, this valve as well as the conventional linear valve requires use of elastomeric gaskets or seals, which gaskets are in contact with the drug and propellant mixture and therefore must be essentially inert with respect to the drug and propellant mixture. As such valves includes several materials being in direct contact with the drug and propellant mixture, regulatory approvals get more complicated

SUMMARY OF THE INVENTION

The object of the invention is to provide a new inhaler valve, which overcomes one or more drawbacks of the prior art. This is achieved by the rotary metering valve, and the method for filling such as defined in the independent claims.

One advantage with the new rotary metering valve is that the actuation angle is very small compared to the prior art rotary metering valve with one metering recess, and that free flow of aerosol formulation is allowed into the metering chamber that will be dispensed in the next actuation of the valve also when the valve comprises a plurality of metering chambers.

Another advantage is that it is simple and well adapted for mass production.

Another advantage is that it is leak proof compared to the prior art rotary metering valve Another advantage is that, in some embodiments, all parts of the valve mechanism that comes in contact with the drug and propellant mixture can be made of the same material and that no elastomeric seals are needed.

Still another advantage is that it can be provided with an extremely reliable and simple counter mechanism for counting the number of doses dispensed through the valve.

Still another advantage is that the rotational motion of the rotary valve in one embodiment is directly connected to a counter mechanism, whereby the counter mechanism becomes truly accurate.

Embodiments of the invention are defined in the dependent claims.

BRIEF DESCRIPTION OF THE DRAWINGS

The invention will be described in detail below with reference to the drawings, in which FIG. 1 schematically shows a cross sectional view of a conventional inhaler can for containing a pharmaceutical substance in a pressurized propellant to be included in an inhalation device.

DETAILED DESCRIPTION OF PREFERRED EMBODIMENTS

Figure 1:
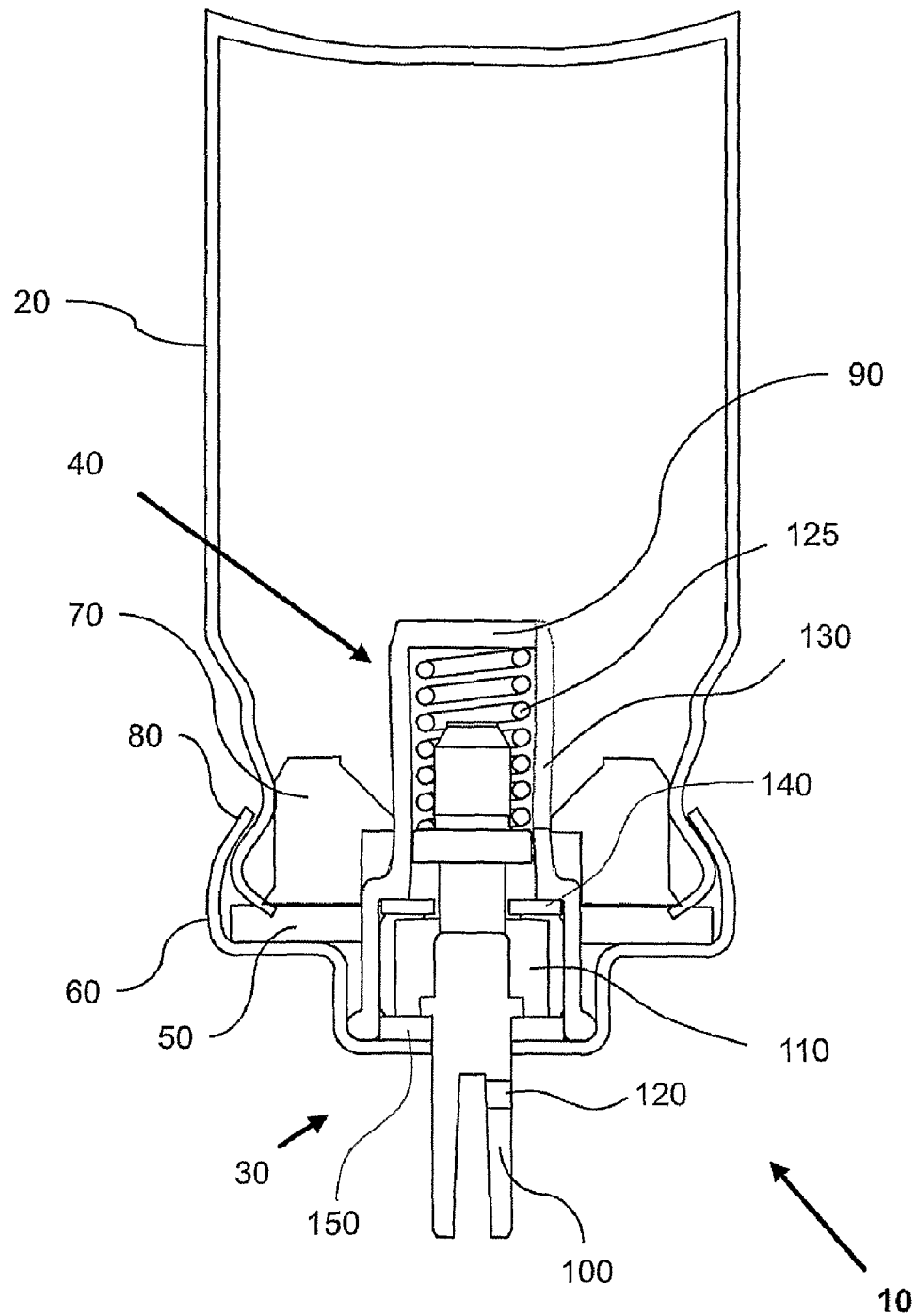
Figure 2A:
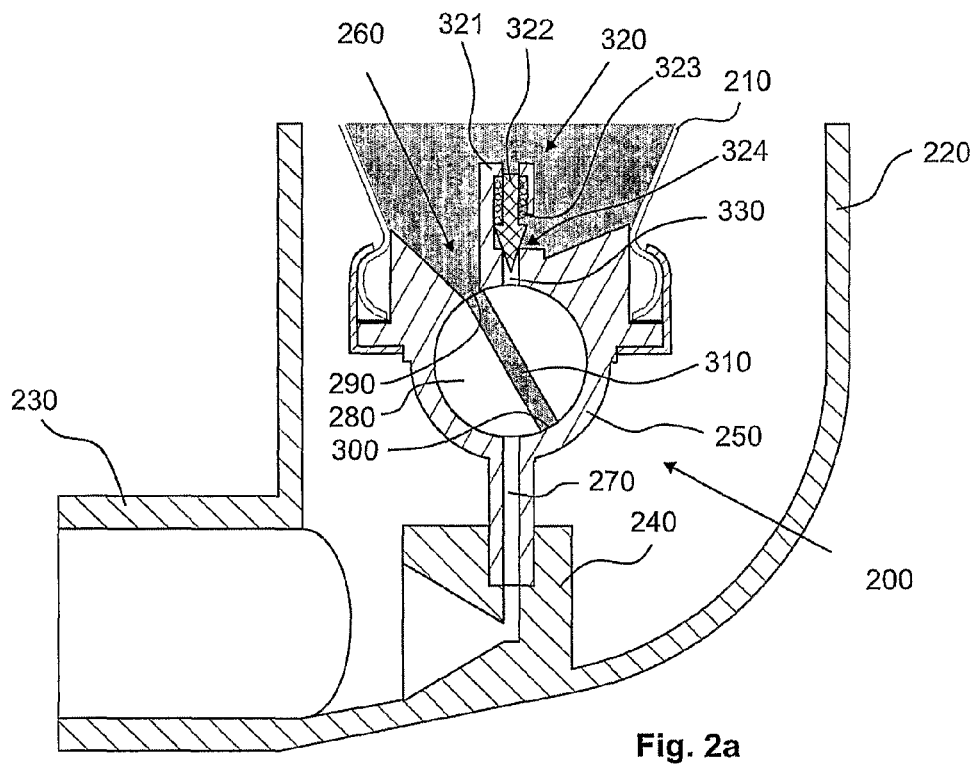
FIGS. 2a to 2c show cross sectional views of one embodiment of a rotary metering valve according to the present invention, and the operation sequence of the valve.
Figure 2B:
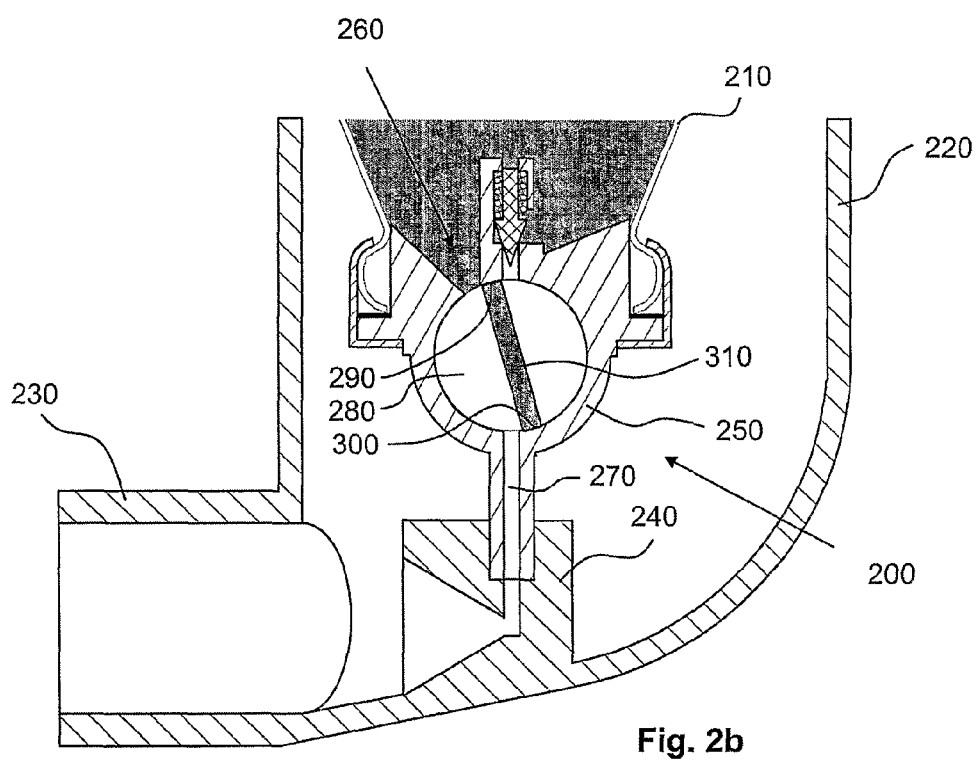
Figure 2C:
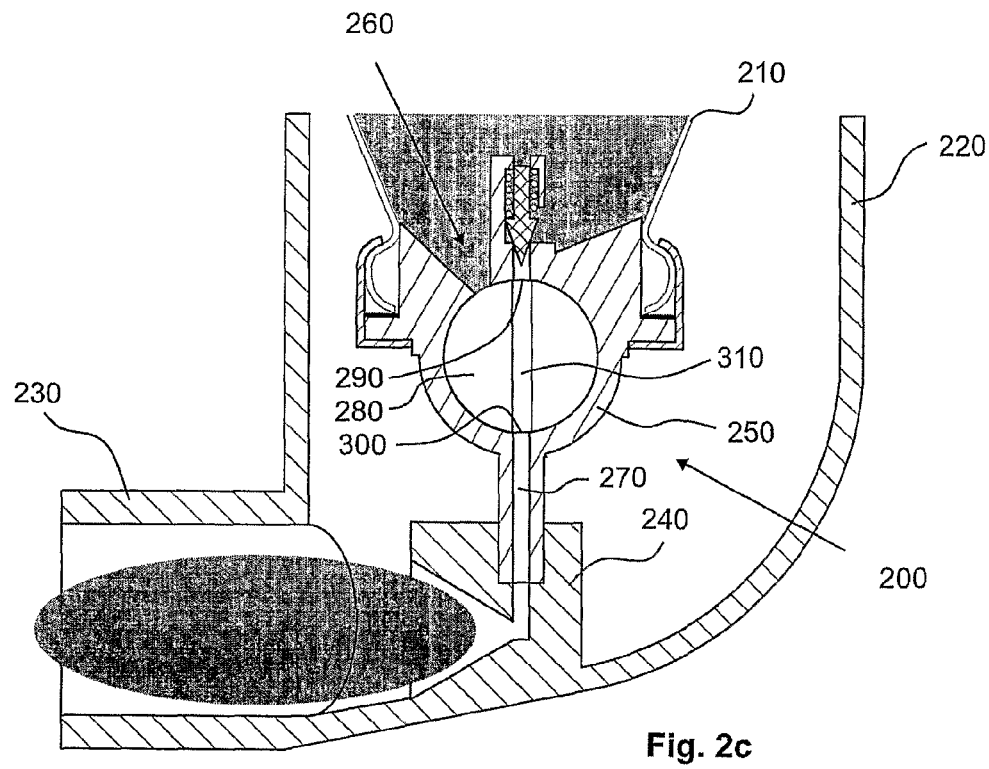

FIGS. 2a to 2c show a schematic cross sectional view of one embodiment of a rotary metering valve 200 according to the present invention. In FIGS. 2a-c, the valve is attached to a canister 210 and the canister and valve assembly thus formed is arranged in an inhaler housing 220 with a mouth piece 230 and a stem receiving nozzle block 240. The valve comprises a valve body 250 shown as one unitary structure in the figure, but which for practical assembly reasons conveniently can be comprised of two parts or more. The valve body 250 comprises a valve inlet 260 in communication with the interior of the canister 210; through which valve inlet 260 the aerosol formulation in the canister enter the rotary metering valve 200. Further, the valve body 250 comprises a valve outlet 270 for dispensing metered volumes of aerosol formulation from the valve. In the disclosed embodiment, the valve outlet 270 is formed as a hollow stem to be inserted into the nozzle block 240, but the valve outlet 270 may be of any suitable design, such as a nozzle or the like. The valve body 250 houses a rotary valve member 280 for transferring a metered dose of aerosol formulation from the valve inlet 260 to the valve outlet 270. The rotary valve member 280 comprises an inlet port 290 and an outlet port 300, both in communication with a metering conduit 310 in the rotary valve member 280. The rotary valve member 280 is in sequence rotatable between at least three positions, shown in sequence by FIGS. 2a to 2c:

FIG. 2a:
    inlet position where the inlet port 290 is in communication with the valve inlet 260 and thus in communication with the aerosol formulation in the canister 210, FIG. 2b:
    metering position where both ports 290 and 300 are closed preserving a metered volume of aerosol formulation in the metering conduit FIG. 2c:
    outlet position where the outlet port 300 is in communication with the valve outlet 270 and the metered volume of aerosol formulation is dispensed from the rotary metering valve 200.

In the embodiment of FIGS. 2a to 2c, the angle of rotation for moving from the inlet position (FIG. 2a) to the outlet position (FIG. 2c), the actuation angle, is approximately 30°. However, depending on the design of the valve, the actuation angle may effectively be selected to any suitable value in the range of 5° to 120°, preferably 5° to 45°, and most preferably 10° to 30°. As discussed above, a large angle is not particularly desirable as it tends to make the actuation mechanism more complex, and it leads to a situation where the inlet 290 and outlet 300 ports, during actuation, travel a long distance along the inner walls of the valve body 250 during which travel the ports must be perfectly sealed resulting in high surface finish requirements and thus increased costs. Hence, it is advantageous to keep the actuation angle small, as long as a sealed metering position is achieved.

According to one embodiment, the rotary valve member 280 is arranged to perform a reciprocating rotational motion between the inlet position and the outlet positions. In an alternative embodiment, discussed in detail below, the rotary valve member 280 is arranged to perform a unidirectional rotational motion, whereby the ports 290, 300 will alternately operate as inlet and outlet port respectively.

Figure 3:
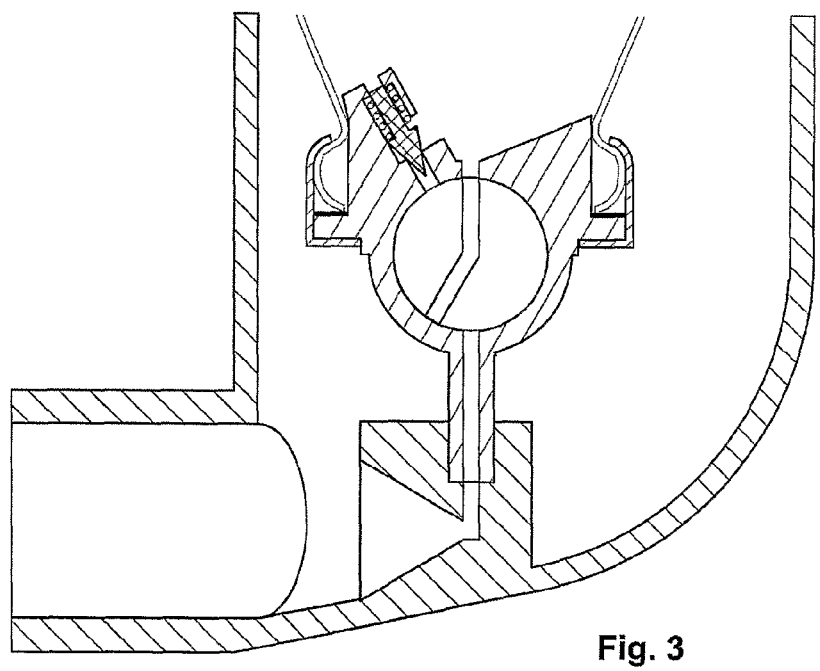
FIG. 3 shows a cross sectional view of another embodiment of a rotary metering valve according to the present invention.

In the disclosed embodiments, the inlet port 290 and the outlet port 300 are arranged diametrically opposite each other with respect to the rotary valve member 280 and that the valve inlet 260 and valve outlet 270 are arranged at an angle of 180° minus the actuation angle. According to one embodiment, the metering conduit 310 is formed by a through-hole straight through the rotary valve member 280 extending between the inlet port 290 and the outlet port 300, respectively. However, as is shown in FIG. 3, the ports may be arranged in other ways, depending on the design of the valve. The rotary metering valve shown in FIG. 3 comprises a "curved" metering conduit 310 that extends from inlet and outlet ports 290, 300 that are not arranged diametrically opposite each other. More in detail, the inlet 290 and outlet 300 ports are arranged at an angle of 180 minus the actuation angle. The embodiment shown in FIG. 3 has the advantage that the valve inlet 260 and valve outlet 270 are aligned, and thus the valve sealing force is maximized for both valve seats.

Figure 4A:
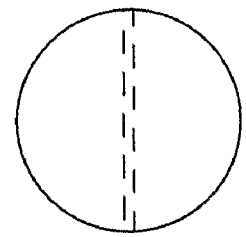
FIGS. 4a to 4e schematically show a number of possible shapes of a rotary valve member.

According to one embodiment, the rotary valve member 280 is of spherical shape, as is shown in FIG. 4*a*. An advantage with a spherical or ball shaped rotary valve member 280 is that it makes it possible to provide valves without use of elastomeric gaskets or seals. Thereby, the rotary metering valve 200 can be made of materials that are proven to be inert with respect to the pharmaceutical propellant mixture. One embodiment of the present invention is a rotary metering valve 200 of the type presented in U.S. Pat. No. 5,772,085, wherein the rotary valve member is of spherical shape, whereby the need for the elastomeric sealing element is eliminated.

The components of the rotary metering valve 200 can be made of any suitable material, but in order to be adapted for mass production they are preferably made of a molded plastic material, such as polyethylene etc.

Figure 4B:
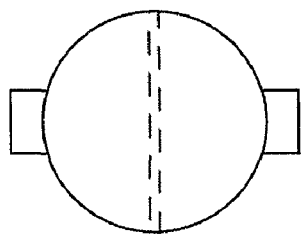
Figure 4C:
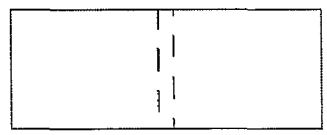
Figure 4D:
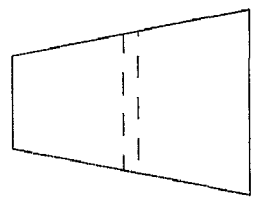
Figure 4E:
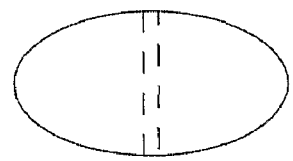

In FIG. 4*b*, the rotary valve member is provided with guide means in order to prevent rotation in other directions than desired. The guide means can be of any suitable shape, such as one or more rotary guides of the type shown in FIG. 4*b* being centered for rotation about the main axis of rotation for the rotary valve member, flange type guide means, or groove type guide means formed in the rotary valve member. FIGS. 4*c* to 4*e* show a number of possible alternative shapes for the rotary valve member, where the rotary valve member shown in:

FIG. 4*c* is a cylinder,

FIG. 4*d* is a truncated cone, and

FIG. 4*e* is an ellipsoid.

In the embodiment of FIGS. 2*a* to 2*c*, the rotary metering valve 200 further comprises a one way filling valve 320 with a filling inlet 300 in communication with the inlet port 290 of the rotary valve member 280 when in the outlet position. According to one embodiment of the present invention, the filling valve comprises a valve housing 321 that preferably is formed as a section of the valve body 250, a valve member 322 and a spring 323. The valve element 322 is biased by the spring 323 towards a valve seat 324, and is thus closed in the rest position. This one way filling valve 320 permits filling of aerosol propellant into the canister without forcing the propellant through any seals or the like, as is the case in the conventional type linear metering valve. Instead, the canister 210 is simply filled by, attaching the source of aerosol to the valve outlet 270, positioning the rotary valve member 280 in the outlet position, and filling the canister 210 through the one way valve 320. In alternative embodiments, the filling of the canister may be performed in alternative ways and the filling valve can be omitted.

Figure 5A:
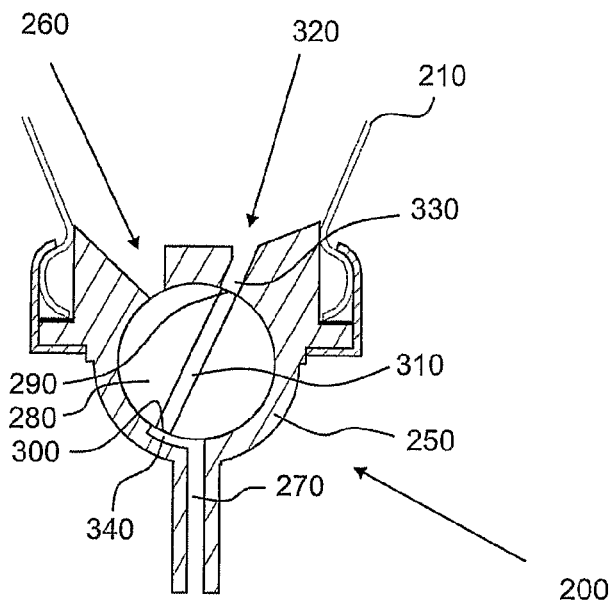
FIGS. 5a and 5b show cross sectional views of two alternative embodiments of rotary metering valves according to the present invention.
Figure 5B:
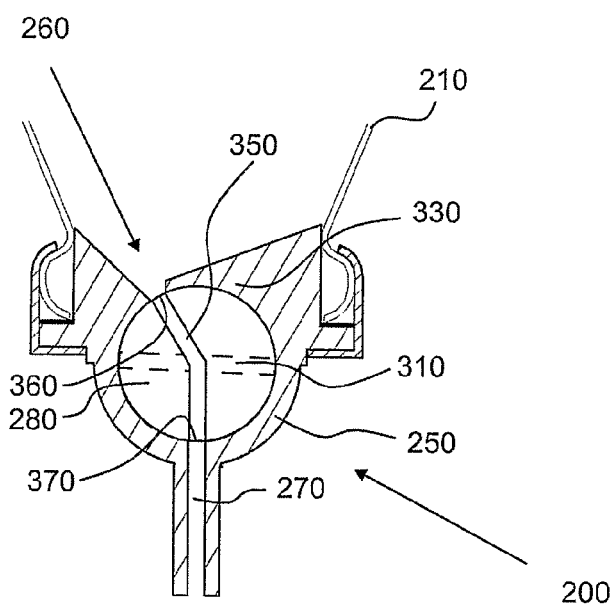
Figure 6C:
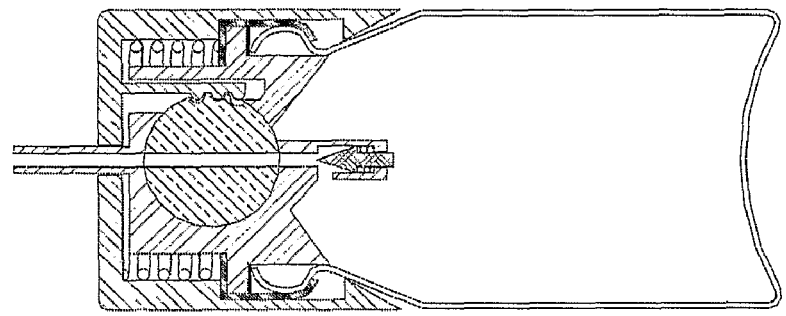
FIGS. 6a to 6c show cross sectional views of still another embodiment of a rotary metering valve according to the present invention, and the operation sequence of the valve.
Figure 6B:
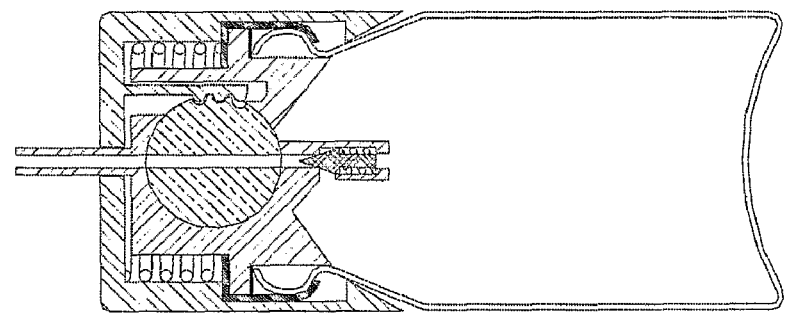
Figure 6A:
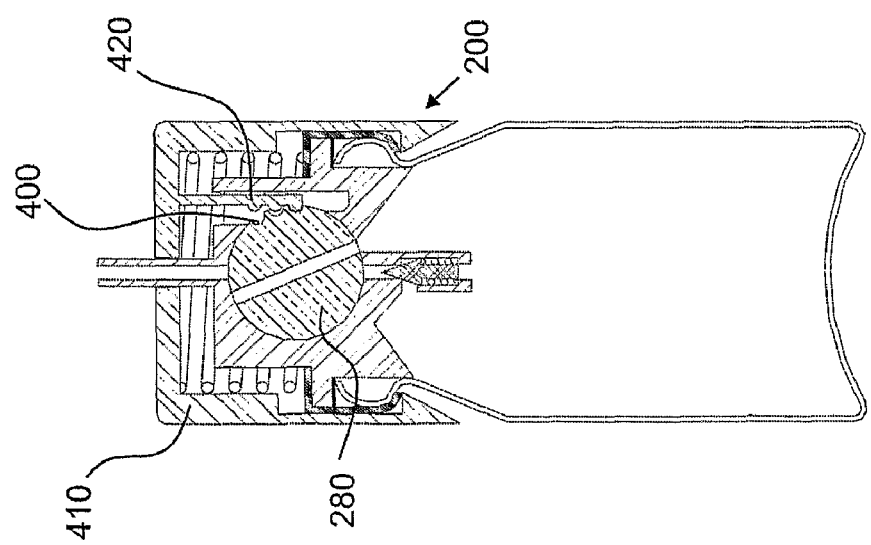
Figure 7:
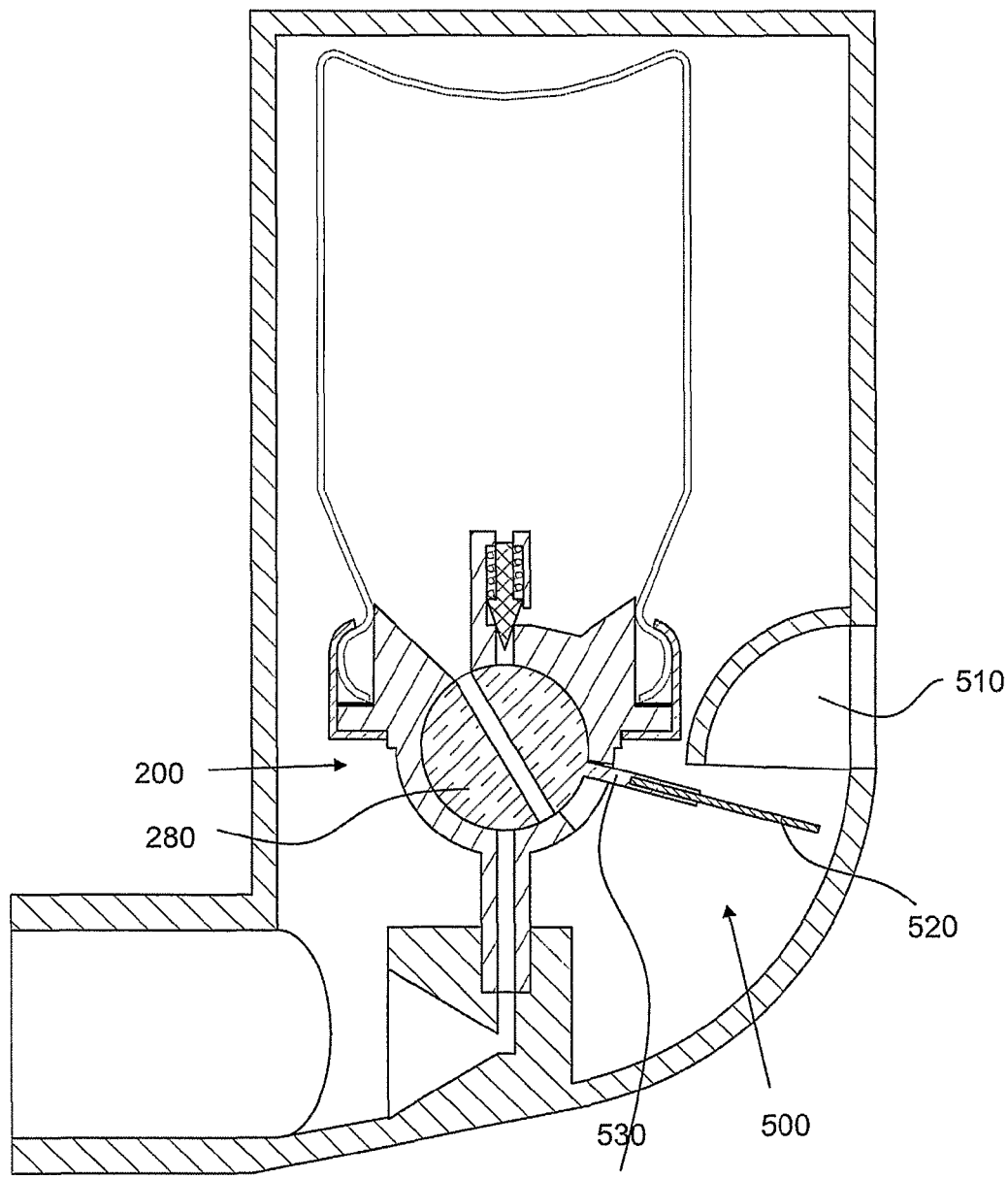
FIG. 7 shows a cross sectional view of still another embodiment of a rotary metering valve according to the present invention comprising a breath actuation mechanism.
Figure 8A:
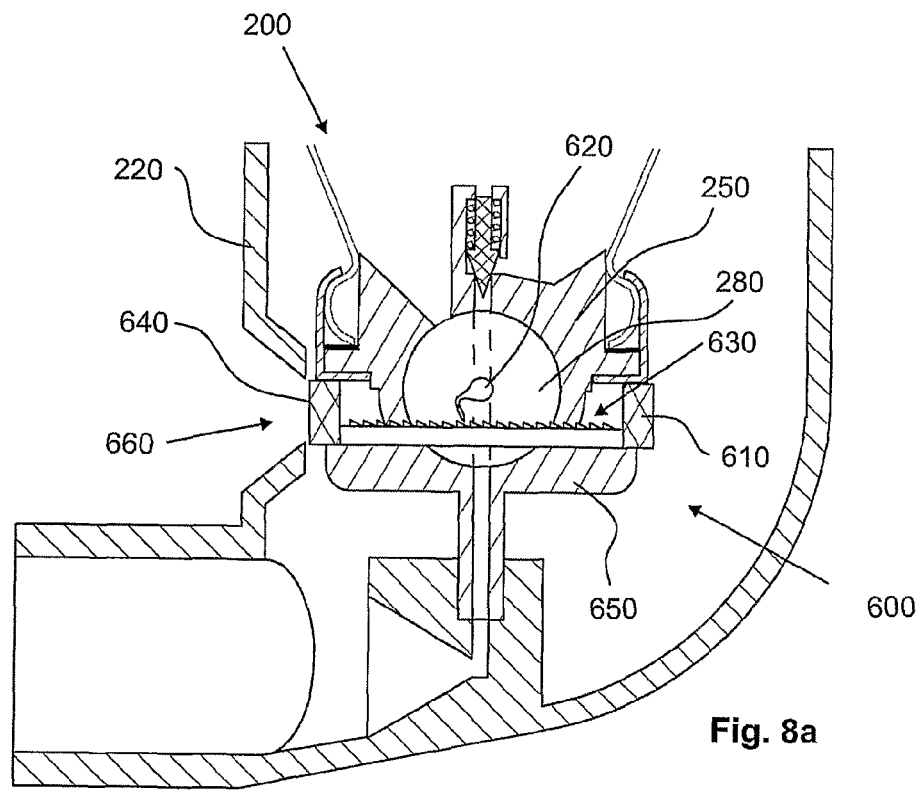
FIGS. 8a and 8b show a schematic cross sectional view of still another embodiment of a rotary valve according to the present invention comprising a dose counter mechanism.
Figure 8B:
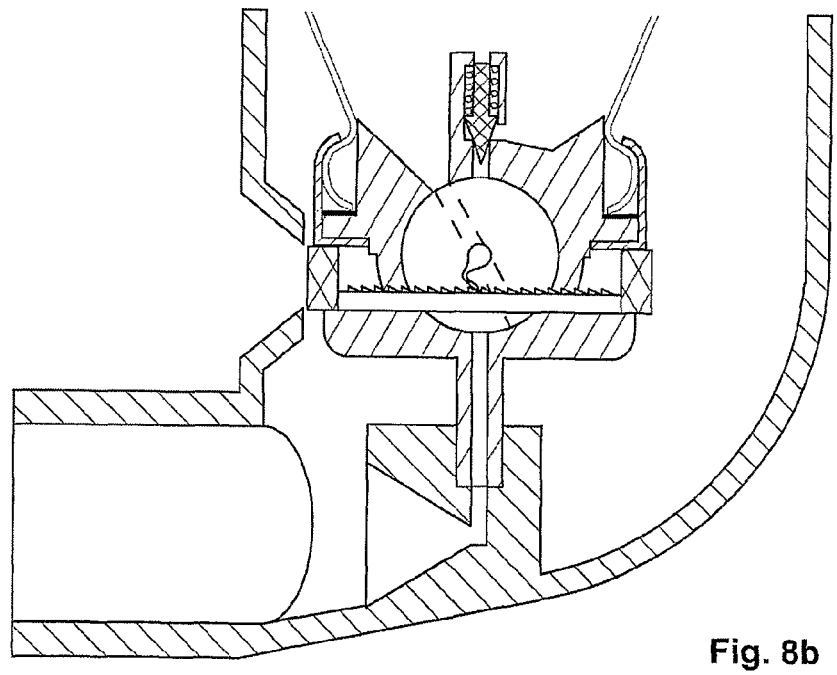
Figure 9:
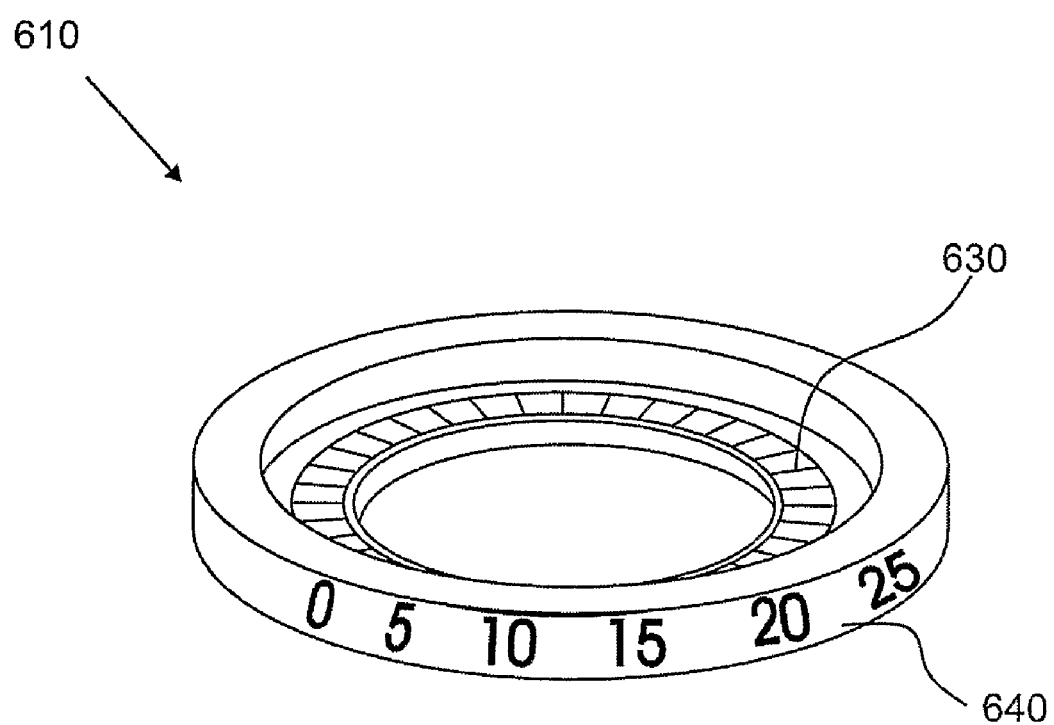
FIG. 9 is a schematic perspective view of a counter display ring.

In one alternative embodiment of the rotary metering valve 200, disclosed in FIG. 5*a*, the rotary valve member 280 is used as filling valve 320. In this embodiment, the valve body 250 is provided with a filling inlet 330, and a filling channel 340 in contact with the valve outlet 270. During filling, the rotary valve member 280 is positioned in a fourth filling position, which position being a restricted position during normal use of the valve, only being accessible for filling the canister 210. When the canister is filled and before the source of aerosol is disconnected from the valve outlet 270, the rotary valve member 280 is rotated to one of the positions of normal use. As is shown in FIG. 4*a*, the filling position can be a position where the rotary valve member 280 is rotated a predetermined angle beyond the inlet or outlet position with respect to the axis of rotation for normal use of the valve. However, in the case the rotary valve member 280 comprises spherical valve surfaces, the filling position could also be at a position that involves rotation of the rotary valve member 280 about an axis of rotation other than the axis of actuation rotation, where after the rotary valve member 280 is restricted to rotation about the axis of actuation rotation.

In still another alternative embodiment of the rotary metering valve 200 disclosed in FIG. 5*b*, the rotary valve member 280 is provided with a filling conduit 350 with inlet and outlet ports 370 and 360 respectively. The ports of the filling conduit 350 being arranged to provide a fill path from the valve outlet 270 to the valve inlet 260 when the rotary valve member 280 is positioned in a filling position like in the above embodiment of FIG. 5*a*.

In the FIGS. 2*a* to 5*b* means for controlling actuation of the valve are omitted in order to keep the figures clear. Actuation of the rotary valve member 280 can be controlled in a number of ways. According to one embodiment the actuation is controlled by a lever means (not shown) connected to the rotary valve member 280. In another embodiment, the actuation is controlled by a link-lever arrangement (not shown) associated with the rotary valve member 280. In still another embodiment, the actuation of the rotary valve member is controlled by a gear arrangement associated with the rotary valve member 280. One embodiment of such a gear arrangement is shown in FIGS. 6*a* to 6*c*, wherein gear teeth 400 have been formed in the rotary valve member 280, and a linear actuation cap 410 is provided with a mating rack gear 420.

FIG. 7 shows a schematic embodiment of a metered dose inhaler with a rotary metering valve 200 according to the present invention provided with breath actuation means 500 for rotation of the rotary valve member 280 to the outlet position. The breath actuation means 500 comprising an air inlet 510 and a throttle member 520 on a lever 530 attached to the rotary valve member 280. When a patient puts the MDI of FIG. 7 to his/her mouth and takes a breath the air stream from the air inlet 510 forces the throttle member 520 and thus the lever 530 to rotate the rotary valve member 280 to the outlet position, whereby the rotary metering valve 200 is actuated and a metered dose of aerosol formulation is inhaled by the patient. Alternatively, the rotary metering valve 200 according to the present invention can be combined with breath actuation mechanisms of other types, such as the mechanisms disclosed in WO 01/70315, WO00/16835, WO01/37909, and WO06/004496.

FIGS. 8*a* and 8*b* schematically shows a rotary metering valve 200 according to the present invention, provided with a dose counter 600. In the disclosed embodiment, the dose counter 600 is comprised of an annular display wheel 610 that surrounds the rotary metering valve 200 and a pawl 620 connected to the reciprocating rotational movement of the rotary valve member 280 for stepwise driving the display wheel 610. As is shown in FIGS. 8*a* and 8*b* and more in detail in FIG. 9 the display wheel 610 comprises an annular ratchet surface 630 for interaction with the pawl 620 and a peripheral indexing surface 640. In FIGS. 8*a* and 8*b*, all parts are shown in cross section, except for the rotary valve member 280 with the pawl 620 and an inner section of the display wheel 610 provided with the annular ratchet surface 630. The valve body 250 is provided with a support structure 650 that supports the display wheel for rotation about the rotary metering valve 200. Just like any conventional pawl/ratchet mechanism the present counter mechanism 600 comprises a back rotation prevention means (not shown) which could be of any suitable type. A display window 660 is provided in the actuator housing 220, whereby the user can read the number of doses present or used. As the disclosed dose counter 600 is fully integrated with the rotary metering valve 200 and the actuation of the dose counter 600 is effected directly by the actuation movement of the rotary valve member 280, it is extremely reliable. Moreover, as the dose counter 600 only involves manufacture and assembly of a few additional components, and possibly only one in case that the pawl is designed as a part of the rotary valve member 280, it is possible to produce at a very low cost. It should also be noted that the direct connection to the rotational movement of the rotary valve member 280 can be used to actuate other types of dose counters in a reliable and effective manner.

Figure 10:
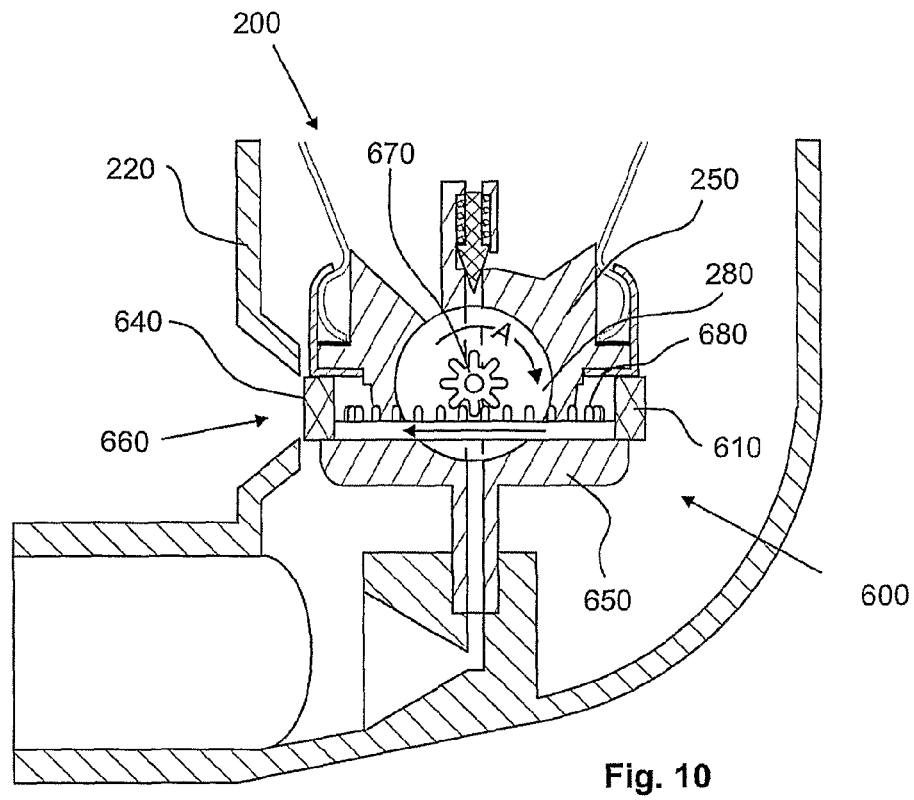
FIG. 10 shows a schematic cross sectional view of still another embodiment of a rotary valve according to the present invention comprising a dose counter mechanism.
Figures 11A, 11B:
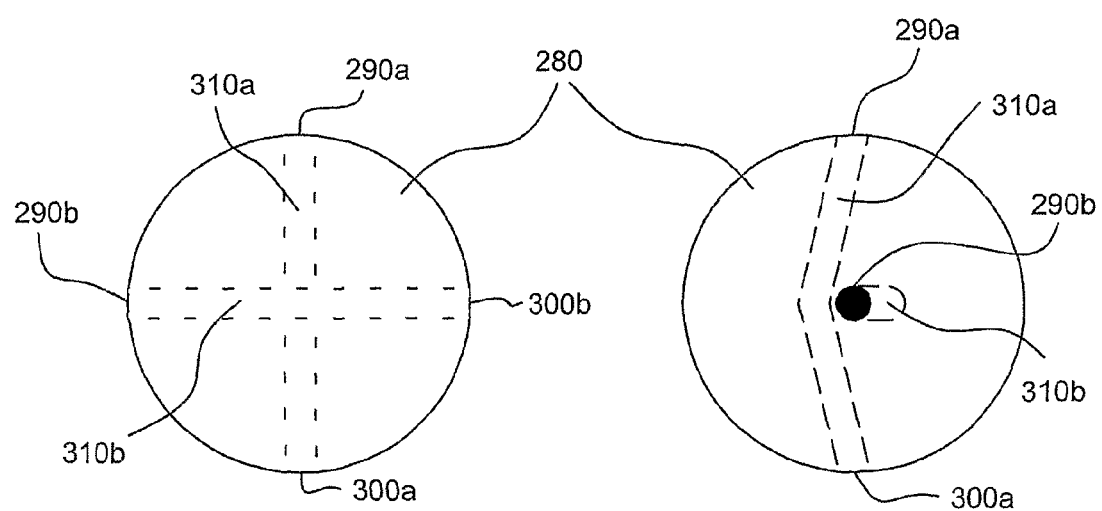
FIGS. 11a and 11b schematically show a rotary valve member comprising two metering conduits.

FIG. 10 schematically shows an alternative embodiment of a rotary metering valve 200 according to the present invention. In this embodiment, the rotational symmetry of the rotary valve member 280 is recognized and the rotary valve member 280 is only allowed to rotate in the direction indicated by the arrow A, i.e. unidirectional rotational movement. In this way the ports 290, 300 connecting the metering conduit 310 in the rotary valve member 280 will alternate as inlet and outlet ports, respectively. As discussed above, the actuation of the rotary metering valve 200 can be performed in numerous ways and will not be described in detail herein. In this embodiment, the rotary valve member 280 has to be rotated 180° between each actuation, but as is shown in FIGS. 11*a* and 11*b* it is possible to reduce the angle of rotation between each subsequent actuation to 90° by providing two separate metering conduits 310*a* and 310*b*, each with two ports 290*a*, 300*a* and 290*b*, 300*b* respectively, in the rotary valve member 280. In this embodiment, all ports 290*a*, 300*a* and 290*b*, 300*b* are arranged so that they are sequentially aligned with the valve inlet 260 and valve outlet 330 respectively, upon rotation of the rotary valve member 280. It is also possible to reduce the angle even more by providing three or more separate metering conduits 310. However, it should be noted that the angle of rotation between the inlet position (FIG. 2*a*) and the outlet position (FIG. 2*b*) still is a relatively small angle, whereby any problems with leakage from the metering conduit 310 effectively are avoided.

One advantage with the rotary metering valve of FIG. 10 is that the one way rotational motion of the rotary valve member 280 can be directly transmitted to a dose counter 600, whereby the counter accuracy will be 100%. One example of a 100% accurate dose counter 600 is shown in FIG. 10, wherein a gear wheel 670 transmits the rotation of the rotary valve member 280 to an annular display wheel 610 provided with a rack of teeth 680 that mate the gear wheel 670. It should be noted that this type of dose counter 600 can be used together with any metering valve with a one way rotary actuation motion.

The invention claimed is:

1. A rotary metering valve, comprising:
   a valve inlet;
   a valve outlet;
   a rotary valve member for transferring a metered dose of pressurized aerosol formulation from the valve inlet to the valve outlet, wherein the rotary valve member is provided with an inlet port and an outlet port, both in communication with a metering conduit in the rotary valve member, the rotary valve member in sequence being rotatable between at least three positions:
   an inlet position where the inlet port is in communication with the valve inlet and pressurized aerosol formulation enters the metering conduit,
   a metering position where both ports are closed preserving a metered volume of pressurized aerosol formulation in the metering conduit, and
   an outlet position where the outlet port is in communication with the valve outlet and the metered dose of pressurized aerosol formulation is dispensed from the valve.

2. The rotary metering valve according to claim 1, wherein the actuation angle of rotation between the inlet position and outlet position is in the range of 5° to 120°.

3. The rotary metering valve according to claim 1, wherein the metering chamber is a hole through the rotary valve member extending between the inlet port and the outlet port, respectively.

4. The rotary metering valve according to claim 1, wherein the inlet and outlet ports are arranged diametrically with respect to the rotary valve member and that the valve inlet and valve outlet are arranged at an angle of 180° minus the actuation angle.

5. The rotary metering valve according to claim 1, wherein the valve inlet and valve outlet are arranged diametrically with respect to the rotary valve member and that the inlet and outlet ports are arranged at an angle of 180minus the actuation angle, and that the metering conduit is curved.

6. The rotary metering valve according to claim 1, further comprising a one way filling valve with a filling port in communication with the inlet port of the rotary valve member when in the outlet position.

7. The rotary metering valve according to claim 6, wherein the one way filling valve includes a valve member that is biased towards a valve seat by a spring so that the filling valve is closed at rest.

8. The rotary metering valve according claim 1, wherein the rotary valve member is rotatable to a filling position at an angle of rotation outside the range of normal operation, said angle being a restricted angle during normal operation of the rotary metering valve.

9. The rotary metering valve according to claim 8, wherein the inlet port is in communication with a filling inlet and that the outlet port is in communication with the valve outlet via a filling channel when the rotary valve member is in the filling position.

10. The rotary metering valve according to claim 8, wherein the rotary valve member includes a filling conduit with inlet and outlet ports, the ports of the filling conduit being arranged to provide a fill path from the valve outlet to the valve inlet when the rotary valve member is positioned in the filling position.

11. The rotary metering valve according to claim 1, wherein the rotary valve member is of spherical shape.

12. The rotary metering valve according to claim 8, wherein the rotary valve member is of spherical shape and that the filling position is arranged at a position that involves rotation of the rotary valve member about an axis of rotation other than the axis of actuation rotation.

13. The rotary metering valve according to claim 1, wherein the rotary valve member has the form of a truncated cone, a cylinder or an ellipsoid.

14. The rotary metering valve according to claim 1, wherein the actuation angle of rotation between the inlet position and outlet position is in the range of 5° to 45°.

15. The rotary metering valve according to claim 1, wherein the actuation angle of rotation between the inlet position and outlet position is in the range of 10° to 30°.

16. The rotary metering valve according to claim 1, wherein the rotation of the rotary valve member is controlled by a lever connected to the rotary valve member.

17. The rotary metering valve according to claim 1, wherein the rotation of the rotary valve member is controlled by a link-lever arrangement associated with the rotary valve member.

18. The rotary metering valve according to claim 1, wherein the rotation of the rotary valve member is controlled by a gear arrangement associated with the rotary valve member.

19. The rotary metering valve according to claim 1, wherein the rotation of the rotary valve member is controlled by a linear gear rack arrangement associated with the rotary valve member.

20. The rotary metering valve according to claim 1, further comprising breath actuation means for rotation of the rotary valve member to the outlet position.

21. The rotary metering valve according to claim 1, wherein the rotary valve member is arranged to perform a reciprocating rotational motion between the inlet position and the outlet positions.

22. The rotary metering valve according to claim 21, wherein the reciprocating motion of the rotary valve member is transferred to a pawl for stepwise driving a dose counter.

23. The rotary metering valve according to claim 22, wherein the pawl is arranged to drive a display wheel with a mating ratchet surface for rotation.

24. The rotary metering valve according to claim 23, wherein the display wheel is annular and surrounds the rotary metering valve.

25. The rotary metering valve according to claim 1, wherein the rotary valve member is arranged to perform a unidirectional rotational motion such that a first pair of ports alternately operate as inlet and outlet port respectively.

26. The rotary metering valve according to claim 25, wherein the unidirectional rotational motion is directly transferred to a counter mechanism.

27. The rotary metering valve according to claim 26, wherein the unidirectional rotational motion is arranged to drive a display wheel via a gear arrangement.

28. The rotary metering valve according to claim 27, wherein the display wheel is annular and surrounds the rotary metering valve.

29. The rotary metering valve according to claim 25, wherein the first pair of ports is interconnected with a first metering chamber,
wherein the rotary valve member having the first pair of ports is provided with at least a second pair of ports, the second pair of ports being interconnected with an associated metering chamber, and
wherein the first and second pairs ports are arranged sequentially aligned with the valve inlet and valve outlet respectively, upon unidirectional rotation of the rotary valve member.

30. An assembly comprising a metered dose inhaler canister and the rotary metering valve according to claim 1 connected to the metered dose inhaler canister.

31. A metered dose inhaler, comprising:
a rotary metering valve according to claim 1; and
a breath actuation portion to rotate the rotary valve member of the rotary metering valve to the outlet position.

32. A rotary metering valve comprising:
a valve inlet;
a valve outlet; and
a rotary valve member for transferring a metered dose of aerosol formulation from the inlet to the outlet, wherein the rotary valve member is of spherical shape.

33. The rotary metering valve according to claim 32, wherein the rotation of the rotary valve member is controlled by a lever connected to the rotary valve member.

34. The rotary metering valve according to claim 32, wherein the rotation of the rotary valve member is controlled by a link-lever arrangement associated with the rotary valve member.

35. The rotary metering valve according to claim 32, wherein the rotation of the rotary valve member is controlled by a gear arrangement associated with the rotary valve member.

36. The rotary metering valve according to claim 32, wherein the rotation of the rotary valve member is controlled by a linear gear rack arrangement associated with the rotary valve member.

37. The rotary metering valve according to claim 32, further comprising breath actuation means for rotation of the rotary valve member to the outlet position.

38. The rotary metering valve according to claim 32, wherein the rotary valve member is arranged to perform a reciprocating rotational motion between the inlet position and the outlet positions.

39. The rotary metering valve according to claim 38, wherein the reciprocating motion of the rotary valve member is transferred to a pawl for stepwise driving a dose counter.

40. The rotary metering valve according to claim 39, wherein the pawl is arranged to drive a display wheel with a mating ratchet surface for rotation.

41. The rotary metering valve according to claim 40, wherein the display wheel is annular and surrounds the rotary metering valve.

42. The rotary metering valve according to claim 32, wherein the rotary valve member is arranged to perform a unidirectional rotational motion such that a first pair of ports alternately operate as inlet and outlet port respectively.

43. The rotary metering valve according to claim 42, wherein the unidirectional rotational motion is directly transferred to a counter mechanism.

44. The rotary metering valve according to claim 43, wherein the unidirectional rotational motion is arranged to drive a display wheel via a gear arrangement.

45. The rotary metering valve according to claim 44, wherein the display wheel is annular and surrounds the rotary metering valve.

46. The rotary metering valve according to claim 42, wherein the first pair of ports is interconnected with a first metering chamber,
wherein the rotary valve member having the first pair of ports is provided with at least a second pair of ports, the second pair of ports being interconnected with an associated metering chamber, and
wherein the first and second pairs ports are arranged sequentially aligned with the valve inlet and valve outlet respectively, upon unidirectional rotation of the rotary valve member.

* * * * *